United States Patent
LaBreck et al.

(10) Patent No.: US 8,174,407 B2
(45) Date of Patent: May 8, 2012

(54) MATERIAL INSPECTION METHODS AND DEVICES

(75) Inventors: Steven Abe LaBreck, Boston, MA (US); Paul Joseph DeAngelo, West Bridgewater, MA (US); Michael Drummy, North Reading, MA (US)

(73) Assignee: Olympus NDT Inc., Waltham, MA (US)

( * ) Notice: Subject to any disclaimer, the term of this patent is extended or adjusted under 35 U.S.C. 154(b) by 442 days.

(21) Appl. No.: 12/477,346

(22) Filed: Jun. 3, 2009

(65) Prior Publication Data

US 2009/0303064 A1 Dec. 10, 2009

Related U.S. Application Data

(60) Provisional application No. 61/058,789, filed on Jun. 4, 2008.

(51) Int. Cl.
*G08B 21/00* (2006.01)

(52) U.S. Cl. ............. 340/945; 73/1.81; 73/1.82; 702/39

(58) Field of Classification Search .................. 340/945; 73/1.78, 1.81, 1.82, 802, 644, 627; 702/34, 702/35, 39

See application file for complete search history.

(56) References Cited

U.S. PATENT DOCUMENTS

| 4,437,332 | A | * | 3/1984 | Pittaro ............................. 73/597 |
| 4,799,177 | A | * | 1/1989 | Sarr ............................... 702/171 |
| 4,840,066 | A | * | 6/1989 | Botsco et al. ................... 73/597 |
| 4,928,257 | A | * | 5/1990 | Yerkes et al. .................... 702/40 |
| 5,285,521 | A | * | 2/1994 | Holt et al. ...................... 704/270 |
| 7,222,514 | B2 | * | 5/2007 | Kollgaard et al. ............. 73/1.82 |
| 2006/0213250 | A1 | * | 9/2006 | Vaccaro et al. ................ 73/1.86 |
| 2007/0084290 | A1 | * | 4/2007 | Fetzer et al. ................... 73/627 |

* cited by examiner

*Primary Examiner* — Brent Swarthout

(74) *Attorney, Agent, or Firm* — Chapin IP Law, LLC

(57) ABSTRACT

Alerting a user of a material inspection device to a change in thickness of a material being inspected is disclosed. A thickness offset is determined from calibration information. The calibration information identifies a time of flight of a pulse through a reference sample similar in composition to a material to be inspected. The thickness offset indicates when a thickness of a material being inspected differs from a thickness of the reference sample. A calibration thickness alarm is set, the calibration thickness alarm corresponding to the thickness offset. A change in thickness of the material being inspected is detected. The calibration thickness alarm is engaged to alert the user of the inspection device of a detected change in thickness of the material being inspected.

22 Claims, 13 Drawing Sheets

401 DETERMINE A THICKNESS OFFSET FROM CALIBRATION INFORMATION, THE CALIBRATION INFORMATION IDENTIFYING A TIME OF FLIGHT OF A PULSE THROUGH A REFERENCE SAMPLE SIMILAR IN COMPOSITION TO A MATERIAL TO BE INSPECTED, THE THICKNESS OFFSET INDICATING WHEN A THICKNESS OF A MATERIAL BEING INSPECTED DIFFERS FROM A THICKNESS OF THE REFERENCE SAMPLE

405 DETERMINE A DAMAGE OFFSET FROM CALIBRATION INFORMATION, THE CALIBRATION INFORMATION IDENTIFYING A TIME OF FLIGHT OF A PULSE THROUGH A REFERENCE SAMPLE SIMILAR IN COMPOSITION TO A MATERIAL TO BE INSPECTED

406 DETERMINE A THICKNESS OFFSET FROM THE DAMAGE OFFSET, THE THICKNESS OFFSET INDICATING WHEN A THICKNESS OF A MATERIAL BEING INSPECTED DIFFERS FROM A THICKNESS OF THE REFERENCE SAMPLE

402 SET A CALIBRATION THICKNESS ALARM, THE CALIBRATION THICKNESS ALARM CORRESPONDING TO THE THICKNESS OFFSET

403 DETECT A CHANGE IN THICKNESS OF THE MATERIAL BEING INSPECTED

407 RECEIVE A RESPONSE ECHO PULSE FROM THE MATERIAL BEING INSPECTED

408 CALCULATE A TIME OF FLIGHT FOR THE RECEIVED RESPONSE ECHO PULSE

409 COMPARE THE CALCULATED TIME OF FLIGHT WITH THE DAMAGE OFFSET AND THE THICKNESS OFFSET TO PRODUCE A RESULT

410 DETECT A CHANGE IN THE THICKNESS OF THE MATERIAL BEING INSPECTED WHEN THE RESULT INDICATES THAT THE CALCULATED TIME OF FLIGHT IS GREATER THAN THE DAMAGE OFFSET AND THE THICKNESS OFFSET

404 ENGAGE THE CALIBRATION THICKNESS ALARM TO ALERT THE USER OF THE INSPECTION DEVICE OF A DETECTED CHANGE IN THICKNESS OF THE MATERIAL BEING INSPECTED

FIG. 4

601 DETERMINE A THICKNESS OFFSET FROM CALIBRATION INFORMATION, THE CALIBRATION INFORMATION IDENTIFYING A TIME OF FLIGHT OF A PULSE THROUGH A REFERENCE SAMPLE SIMILAR IN COMPOSITION TO A MATERIAL TO BE INSPECTED, THE THICKNESS OFFSET INDICATING WHEN A THICKNESS OF A MATERIAL BEING INSPECTED DIFFERS FROM A THICKNESS OF THE REFERENCE SAMPLE

602 SET A CALIBRATION THICKNESS ALARM, THE CALIBRATION THICKNESS ALARM CORRESPONDING TO THE THICKNESS OFFSET

603 DETECT A CHANGE IN THICKNESS OF THE MATERIAL BEING INSPECTED

604 ENGAGE THE CALIBRATION THICKNESS ALARM TO ALERT THE USER OF THE INSPECTION DEVICE OF A DETECTED CHANGE IN THICKNESS OF THE MATERIAL BEING INSPECTED

605 PRIOR TO DETECTING, PROVIDE A GRAPHICAL USER INTERFACE TO THE USER, THE GRAPHICAL USER INTERFACE CAPABLE OF PRESENTING A RECEIVED RESPONSE ECHO PULSE AND INFORMATION CONCERNING THE MATERIAL BEING INSPECTED

606 AUTOMATICALLY AMPLIFY AN AMPLITUDE OF THE RECEIVED RESPONSE ECHO PULSE TO OPTIMIZE THE RECEIVED RESPONSE ECHO PULSE IN REGARDS TO A RANGE OF THE INSPECTION DEVICE SHOWN ON THE GRAPHICAL USER INTERFACE

607 AUTOMATICALLY APPLY A TIME-VARIED GAIN TO A FIRST RECEIVED RESPONSE ECHO PULSE AND A SECOND RECEIVED RESPONSE ECHO PULSE TO OPTIMIZE THE FIRST RECEIVED RESPONSE ECHO PULSE AND THE SECOND RECEIVED RESPONSE ECHO PULSE IN REGARDS TO A RANGE OF THE INSPECTION DEVICE SHOWN ON THE GRAPHICAL USER INTERFACE

FIG. 6

Pulse-echo transducer configuration

Through-transmission transducer configuration

MATERIAL INSPECTION METHODS AND DEVICES

CROSS REFERENCE TO RELATED APPLICATIONS

The present application claims the benefit of U.S. Provisional Patent Application No. 61/058,789 filed on Jun. 4, 2008; which is incorporated herein by reference in its entirety.

BACKGROUND

Materials suffer damage over time. For example, an airplane fuselage is typically composed of a composite material, particularly in the area surrounding the passenger entry/exit doors. When a boarding ramp comes into contact with such an area, the impact of the ramp against the fuselage may cause tiny amounts of internal fractures within the material. This is especially true if the boarding ramp was moving too fast upon impact. Though superficial damage to the surface of the material may also result, such visible damage is a poor indication of whether or not sub-surface damage is present, or an amount of such sub-surface damage.

Thus, techniques and devices have been developed to test materials for such sub-surface damage. One such device is described in U.S. Pat. No. 7,222,514 to Kollgaard et al. The Kollgaard device includes a calibration mode and a test mode. During calibration, the device is applied to a surface of an object that is similar in composition to a composite material to be tested. Said object is referred to as the 'reference sample'. The device transmits an ultrasonic pulse (which may otherwise be referred to herein as a calibration pulse, or merely a pulse) to the reference sample. This causes a return echo pulse to travel through the reference sample back to the device. Such a return echo pulse is a reflection of the originally transmitted ultrasonic pulse due to a mismatch in the acoustic impedance between the rear surface of the reference sample and the adjacent air. The amplitude of the return echo pulse and the time of flight (i.e., the time from when the device transmits the calibration pulse through the front surface of the material to the time when the device receives the return echo) are stored as calibration readings. Other aspects of the return echo pulse, such as signal envelope, may also be stored. Typically, however, only the time of flight is needed.

In test mode, the Kollgaard device is applied to the material to be tested, and an ultrasonic pulse is sent through that material. If a return echo pulse comes back to the device in less time than the calibration readings indicate a pulse should need to reach the back end of the material and return, and perhaps with a change in amplitude, the device informs the user that sub-surface damage may be present in that location. That location is noted and later tested using more advanced methods, so as to determine whether or not the material needs to be repaired or replaced, or if structure containing the material is safe for use. Note that if there is a large amount of subsurface damage within the material, a return echo pulse may not be detected due to the damage preventing a sufficient amount of pulse energy from reaching the device. Alternatively, if a return echo pulse comes back to the device having the same or similar amplitude and time of flight as the calibration pulse, then sub-surface damage is likely not present in the material.

The Kollgaard device informs a user of possible sub-surface damage through use of one or more light-emitting diodes (LEDs). If sub-surface damage is detected, one LED is illuminated; if there is no sub-surface damage, another LED is illuminated. Further, other information, such as the depth of damage, and whether the device is calibrated or not, is also shown through LED illumination. The Kollgaard device does not provide any other data, or more specific data, relating to possible damage present in the material.

SUMMARY

Conventional composite material inspection devices such as those described above suffer from a variety of deficiencies. One such deficiency arises when the material under inspection is of non-uniform thickness. For example, typically the outer portion of an airplane is composed of a material. This material is of a first thickness around the frame primary passenger entry/exit door, but is of a second thickness at a distance away from the frame of the door. Conventional material inspection devices do not provide any indication that an operator has moved the inspection device to an area of material that has a different thickness than the reference sample used to calibrate the conventional device. As a result, the operator of the conventional inspection device may be receiving inaccurate readings that indicate, for example, subsurface damage in the material where no such damage exists. Such inaccurate readings result from the operator unknowingly testing a portion of the material that has a different thickness than the reference sample used to calibrate the conventional device. Time and resources may then be wasted, both in performing further tests on material that is otherwise fine, and in the operator of the device having to inspect the material again.

Embodiments disclosed herein overcome such deficiencies by providing for an improved inspection of material that alerts an operator when the thickness of the material under inspection is different than the thickness of a calibration reference sample. After the typical calibration process described above is performed on a reference material, a thickness offset is determined. The thickness offset identifies a point in time in relation to the time of flight of the calibration pulse. If a return echo pulse is received after that point in time, then the material being tested is of a different thickness than the reference sample used during calibration. An operator testing the material is alerted of this change in thickness, which is otherwise not visible to the operator. The operator, in response, moves the testing apparatus to a different location on the material being tested, and performs the test again. The operator may repeat this process until the testing apparatus is again testing material of the same thickness as the reference sample. The operator is thus able to ignore readings that would, on conventional devices, indicate sub-surface damage where in fact no sub-surface damage may exist, or that, on current embodiments, indicate that the inspection measurement was made in an invalid thickness region of the object under test.

Further, embodiments disclosed herein also improve on display and control aspects of conventional devices, such as the Kollgaard device described above. For example, as described above, the Kollgaard device provides information in the form of LEDs that are illuminated. An operator of the Kollgaard device never sees a graphical representation of any pulse used throughout the inspection process. By providing such a graphical representation, embodiments may increase an operator's confidence in the data, particularly when the operator sees unusual data. Additionally, a more robust graphical display of data, such as a graphical user interface, allows embodiments to present an operator with more advanced options for operation and control of the improved device. Finally, a conventional device such as the Kollgaard device does not include automatically adjusting the gain to optimize it for measurement of return echo pulses, or increasing the gain over time in order to compensate for ultrasonic signal amplitude attenuation or wide excursion of amplitudes of return echo pulses. Embodiments disclosed herein provide for such improvements.

More particularly, in an embodiment, there is provided a method of alerting a user of a material inspection device of a change in thickness of a material being inspected. The method includes determining a thickness offset from calibration information, the calibration information identifying a time of flight of a pulse through a reference sample similar in composition to a material to be inspected, the thickness offset indicating when a thickness of a material being inspected differs from a thickness of the reference sample. The method also includes setting a calibration thickness alarm, the calibration thickness alarm corresponding to the thickness offset, detecting a change in thickness of the material being inspected, and engaging the calibration thickness alarm to alert the user of the inspection device of a detected change in thickness of the material being inspected.

In a related embodiment, detecting may include receiving a response echo pulse from the material being inspected; calculating a time of flight for the received response echo pulse; comparing the calculated time of flight with the time of flight through the reference sample and the thickness offset to produce a result; and detecting a change in the thickness of the material being inspected when the result indicates that the calculated time of flight is greater than the time of flight through the reference sample and the thickness offset.

In another related embodiment, determining may include determining a damage offset from calibration information, the calibration information identifying a time of flight of a pulse through a reference sample similar in composition to a material to be inspected; and determining a thickness offset from the damage offset, the thickness offset indicating when a thickness of a material being inspected differs from a thickness of the reference sample. In a further related embodiment, detecting may include receiving a response echo pulse from the material being inspected; calculating a time of flight for the received response echo pulse; comparing the calculated time of flight with the damage offset and the thickness offset to produce a result; and detecting a change in the thickness of the material being inspected when the result indicates that the calculated time of flight is greater than the damage offset and the thickness offset.

In yet another related embodiment, engaging may include providing a graphical user interface that presents the calibration thickness alarm to the user of the inspection device; and engaging the calibration thickness alarm to alert the user of the inspection device of a change in thickness of the material being inspected. In a further related embodiment, providing may include providing a graphical user interface that presents a waveform of a received response echo pulse, the calibration information, and the calibration thickness alarm to the user of the inspection device.

In still another related embodiment, the method may include prior to detecting, providing a graphical user interface to the user, the graphical user interface capable of presenting a received response echo pulse and information concerning the material being inspected. In a further related embodiment, the method may include automatically amplifying an amplitude of the received response echo pulse to optimize the received response echo pulse in regards to a range of the inspection device shown on the graphical user interface. In yet another further related embodiment, the method may include automatically applying a time-varied gain to a first received response echo pulse and a second received response echo pulse to optimize the first received response echo pulse and the second received response echo pulse in regards to a range of the inspection device shown on the graphical user interface.

In another embodiment, there is provided a material inspection device. The material inspection device includes an offset calculator, the offset calculator determining a thickness offset from calibration information, the calibration information identifying a time of flight of a pulse through a reference sample similar in composition to a material to be inspected, the thickness offset indicating when a thickness of a material being inspected differs from a thickness of the reference sample. The material inspection device also includes a memory unit, the memory unit storing the calibration information received by the data receiving unit and the thickness offset determined by the offset calculator; a detector, the detector configured to detect a change in thickness of the material being inspected; and a calibration thickness alarm, the calibration thickness alarm set corresponding to the thickness offset stored in the memory unit, that when engaged, alerts a user of the device of a change in thickness of the material as detected by the detector.

In another embodiment, there is provided a computer program product, stored on computer readable medium, for alerting a user of a material inspection device of a change in thickness of a material being inspected. The computer program product includes computer program code for determining a thickness offset from calibration information, the identifying a time of flight of a pulse through a reference sample similar in composition to a material to be inspected, the thickness offset indicating when a thickness of a material being inspected differs from a thickness of the reference sample; computer program code for setting a calibration thickness alarm, the calibration thickness alarm corresponding to the thickness offset; computer program code for detecting a change in thickness of the material being inspected; and computer program code for engaging the calibration thickness alarm to alert the user of the inspection device of a detected change in thickness of the material being inspected.

In another embodiment, there is provided a computer system. The computer system includes a memory, a processor, a display, an input/output interface, and an interconnection mechanism coupling the memory, the processor, and the input/output interface, allowing communication there between. The memory of the computerized device is encoded with a calibration thickness alarm application, that when executed in the processor, provides a calibration thickness alarm process that alerts a user of a material inspection device of a change in thickness of a material being inspected, by causing the computer system to perform operations of: determining a thickness offset from calibration information, the identifying a time of flight of a pulse through a reference sample similar in composition to a material to be inspected, the thickness offset indicating when a thickness of a material being inspected differs from a thickness of the reference sample; setting a calibration thickness alarm, the calibration thickness alarm corresponding to the thickness offset; detecting a change in thickness of the material being inspected; and engaging the calibration thickness alarm to alert the user of the inspection device of a detected change in thickness of the material being inspected.

Other arrangements of embodiments of the invention that are disclosed herein include software programs to perform the method embodiment steps and operations summarized above and disclosed in detail below. More particularly, a computer program product is one embodiment that has a computer-readable medium including computer program logic encoded thereon that when performed in a computerized device provides associated operations providing client management of download sequence of orchestrated content as explained herein. The computer program logic, when executed on at least one processor with a computing system, causes the processor to perform the operations (e.g., the methods) indicated herein as embodiments of the invention. Such arrangements of the invention are typically provided as software, code and/or other data structures arranged or encoded on a computer readable medium such as but not limited to an optical medium (e.g., CD-ROM, DVD-ROM, etc.), floppy or hard disk, a so-called "flash" (i.e., solid state) memory medium, or other physical medium, such as but not limited to firmware or microcode in one or more ROM or RAM or PROM chips, or as an Application Specific Integrated Circuit (ASIC), or as downloadable software images in one or more modules, shared libraries, etc. The software or firmware or other such configurations can be installed onto a computerized device to cause one or more processors in the computerized device to perform the techniques explained herein as embodiments of the invention. Software processes that operate in a collection of computerized devices, such as in a group of data communications devices or other entities may also provide the system of the invention. The system of the invention may be distributed between many software processes on several data communications devices, or all processes may run on a small set of dedicated computers, or on one computer alone.

It is to be understood that embodiments of the invention may be embodied strictly as a software program, as software and hardware, or as hardware and/or circuitry alone. The features disclosed and explained herein may be employed in computerized devices and software systems for such devices such as those manufactured by Olympus NDT Inc. of Waltham, Mass.

BRIEF DESCRIPTION OF THE DRAWINGS

The foregoing will be apparent from the following description of particular embodiments disclosed herein, as illustrated in the accompanying drawings in which like reference characters refer to the same parts throughout the different views. The drawings are not necessarily to scale, emphasis instead being placed upon illustrating the principles disclosed herein.

FIG. 4 illustrates a flowchart of a procedure performed by the system of FIG. 1 when alerting a user of a detection of a difference in thickness of a material being inspected due to an offset from an identifier of damage in the material.

FIG. 6 illustrates a flowchart of a procedure performed by the system of FIG. 1 when providing controls and other data for a material inspection device via a graphical user interface.

DETAILED DESCRIPTION

Figure 1:
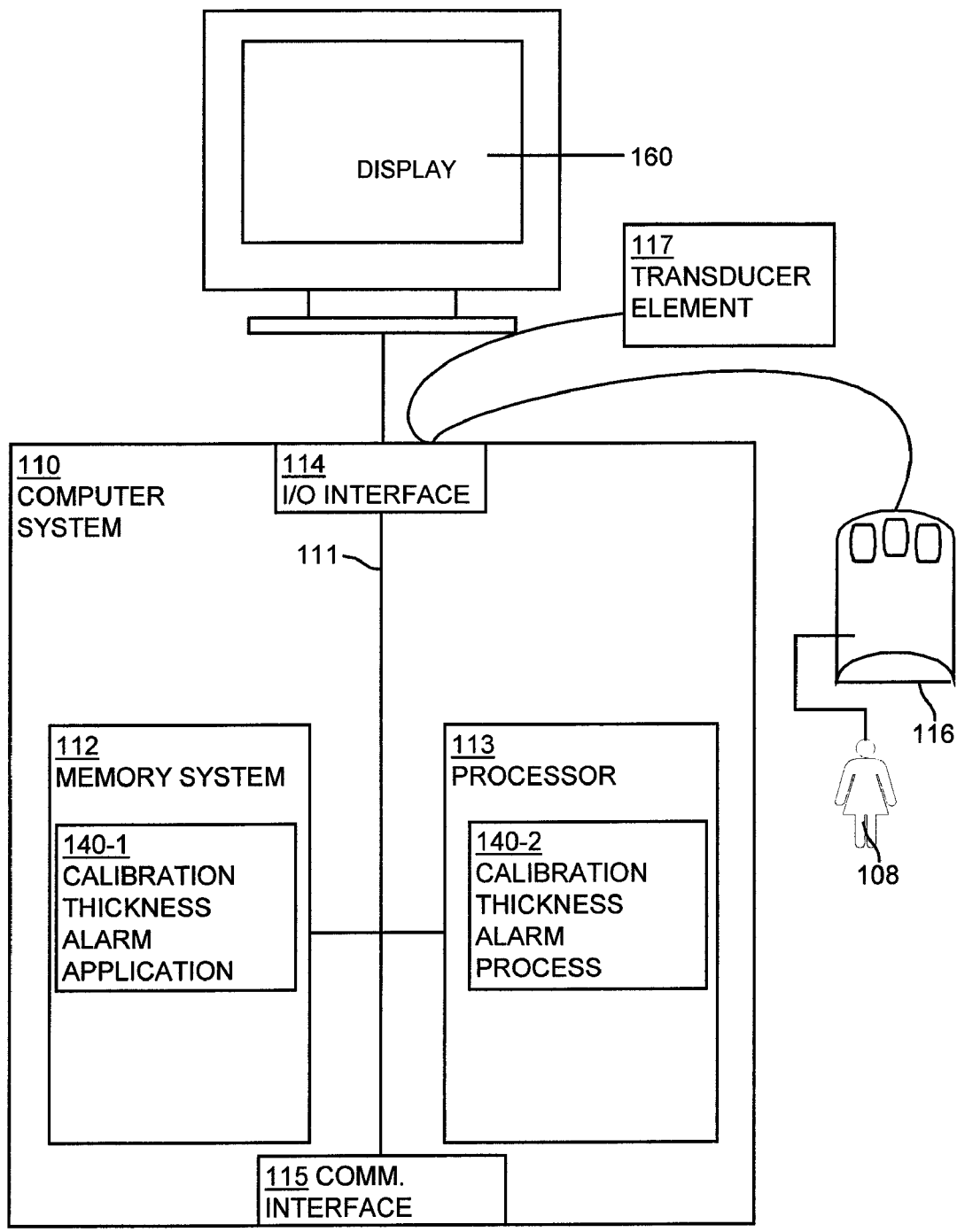
FIG. 1 shows a high-level block diagram of a computer system according to one embodiment disclosed herein.

Generally, disclosed embodiments provide improved methods and apparatus for, during inspection of material for sub-surface damage, alerting a user that the thickness of the material being inspected is different from the thickness of the material used during calibration. Typically, for calibration purposes, an ultrasonic pulse is sent through a reference sample that is of the same thickness as a material to be inspected. This generates a return echo pulse of a given amplitude, which takes a particular time to travel through the reference sample and back (i.e., time of flight). Note that the terms "sub-surface damage" and "flaw" used herein may be used interchangeably. That is, as used herein, a sub-surface damage/flaw generally refers to a condition within the material under test that is not intended to be present (e.g. a delamination, crack, void, porosity, etc). Note also that the terms "pulse", "ultrasonic pulse", and "echo pulse" used herein may be used interchangeably. That is, as used herein, a pulse/ultrasonic pulse/echo pulse generally refers to a burst of energy (typically ultrasonic energy) applied by a transducer to an object, such as a material, that travels through the object until it meets an area of substantially different acoustic impedance (e.g., an area of sub-surface damage, the rear wall of the object, etc.), at which point the pulse may be reflected back, resulting in a return of the energy to the transducer. Further note that the time of flight of a pulse may be expressed in terms of thickness units (e.g. inches, millimeters) by using the velocity of the pulse travelling through the material to calculate thickness, as described herein. If the return echo pulse of the inspected material is equivalent to, or in close range of, the amplitude and/or the time of flight of the return pulse received during calibration, no damage is present. If the time of flight and/or amplitude of the return echo pulse differ (outside the close range) from the calibration data, however, sub-surface damage is likely present. In some situations, the difference in time of flight and/or amplitude may actually result from a change in thickness of the material, which an operator of a testing apparatus is unable to see. Embodiments determine a thickness offset that allows for determining if a return echo pulse is indicative of damage, or a change in thickness. If a change in thickness occurs, a user of the device is alerted so that the user is able to locate the device in an area of the material to be tested that is of the same (or similar) thickness as the reference sample used for calibration. Disclosed embodiments also provide for graphical displays of data relating to detected damage and changes in thickness, including graphical warning of changes in thickness, and include automatic gain controls to adjust data for optimal showing on such a graphical display.

Ultrasonic transducers are devices that convert electrical energy to mechanical energy, or vice versa. An electric potential is created across a piezoelectric element, exciting the element at a frequency corresponding to the applied voltage. As a result, the piezoelectric element emits an ultrasonic beam of acoustic energy that may be coupled into a material under test. Conversely, when an acoustic wave, an echo of the original ultrasonic beam for example, strikes the piezoelectric element, the element will produce a corresponding voltage across its electrodes.

Thus, as used herein, the terms "material inspection device" and "inspection device" may refer to an overall device that includes a transducer element and a gauge for display of readings or may refer to only the transducer element of such a device.

Further, note that as used herein, the terms "object" and "material" may be used interchangeably throughout, and may include a laminate structure, a composite material, or any other type of structure or material that may be inspected using an inspection device.

More particularly, FIG. 1 is a block diagram illustrating example architecture of a computer system 110 that executes, runs, interprets, operates or otherwise performs a calibration thickness alarm application 140-1 and a calibration thickness alarm process 140-2 suitable for use in explaining example configurations disclosed herein. The computer system 110 may be any type of computerized device such as a personal computer, workstation, portable computing device, console, laptop, network terminal or the like, an in some embodiments, is a material inspection device as disclosed and described herein, which may include a transducer element 117. As shown in this example, the computer system 110 includes an interconnection mechanism 111 such as a data bus or other circuitry that couples a memory system 112, a processor 113, an input/output interface 114, and may include (as shown) a communications interface 115. An input device 116 (e.g., one or more user controlled devices such as a keyboard, mouse, touchpad, trackball, etc.) couples to the processor 113 through the I/O interface 114 and enables a user 108 to provide input commands and, in some embodiments, to generally control a graphical user interface 160 shown on a display device 130. In some embodiments, the communications interface 115 may enable the computer system 110 to communicate with other devices (e.g., other inspection devices) on a network (that is not shown in FIG. 1).

The memory system 112 is any type of computer readable medium and in this example is encoded with a calibration thickness alarm application 140-1. The calibration thickness alarm application 140-1 may be embodied as software code such as data and/or logic instructions (e.g., code stored in the memory or on another computer readable medium such as a removable disk) that supports processing functionality according to different embodiments described herein. During operation of the computer system 110, the processor 113 accesses the memory system 112 via the interconnection mechanism 111 in order to launch, run, execute, interpret or otherwise perform the logic instructions of the calibration thickness alarm application 140-1. Execution of the calibration thickness alarm application 140-1 in this manner produces processing functionality in a calibration thickness alarm process 140-2. In other words, the calibration thickness alarm process 140-2 represents one or more portions or runtime instances of the calibration thickness alarm application 140-1 performing or executing within or upon the processor 113 in the computer system 110 at runtime.

It is noted that example configurations disclosed herein include the calibration thickness alarm application 140-1 itself including the calibration thickness alarm process 140-2 (i.e., in the form of un-executed or non-performing logic instructions and/or data). The calibration thickness alarm application 140-1 may be stored on a computer readable medium (such as a floppy disk), hard disk, electronic, magnetic, optical or other computer readable medium. The calibration thickness alarm application 140-1 may also be stored in a memory system 112 such as in firmware, read only memory (ROM), or, as in this example, as executable code in, for example, Random Access Memory (RAM). In addition to these embodiments, it should also be noted that other embodiments herein include the execution of the calibration thickness alarm application 140-1 in the processor 113 as the calibration thickness alarm process 140-2. Those skilled in the art will understand that the computer system 110 may include other processes and/or software and hardware components, such as an operating system not shown in this example.

The display 130 need not be coupled directly to computer system 110. For example, the calibration thickness alarm application 140-1 may be executed on a remotely accessible computerized device via the network interface 115. In this instance, the graphical user interface 160 may be displayed locally to a user of the remote computer and execution of the processing herein may be client-server based. In some embodiments, the graphical user interface 160 may be an operator interface through which a user, such as the user 108, is able to view information of different types and take various actions. The amount of features, and control thereof, may depend on a user level, such that a basic user has access to only a certain amount of features, while an administrator may have access to all available features. Key features of the graphical user interface 160 are described herein with regards to FIGS. 5 and 6.

FIGS. 2A-2D illustrate examples of material upon which the calibration thickness alarm process 140-2 may operate. FIGS. 3-6 are flowcharts of various embodiments of the calibration thickness alarm process 140-2. The rectangular elements are herein denoted "processing blocks" and represent computer software instructions or groups of instructions. Alternatively, the processing blocks represent steps performed by functionally equivalent circuits such as a digital signal processor circuit or an application specific integrated circuit (ASIC). The flowcharts do not depict the syntax of any particular programming language. Rather, the flowcharts illustrate the functional information one of ordinary skill in the art requires to fabricate circuits or to generate computer software to perform the processing required in accordance with the present invention. It should be noted that many routine program elements, such as initialization of loops and variables and the use of temporary variables are not shown. It will be appreciated by those of ordinary skill in the art that unless otherwise indicated herein, the particular sequence of steps described is illustrative only and may be varied without departing from the spirit of the invention. Thus, unless otherwise stated, the steps described below are unordered, meaning that, when possible, the steps may be performed in any convenient or desirable order. FIGS. 7A-7B and FIGS. 8A-8H illustrate examples of an interface as shown on a display of a material inspection application. FIGS. 9A-9B illustrate example block diagrams of a material inspection device where gain is used to optimally present information to an operator of the device.

Figure 3:
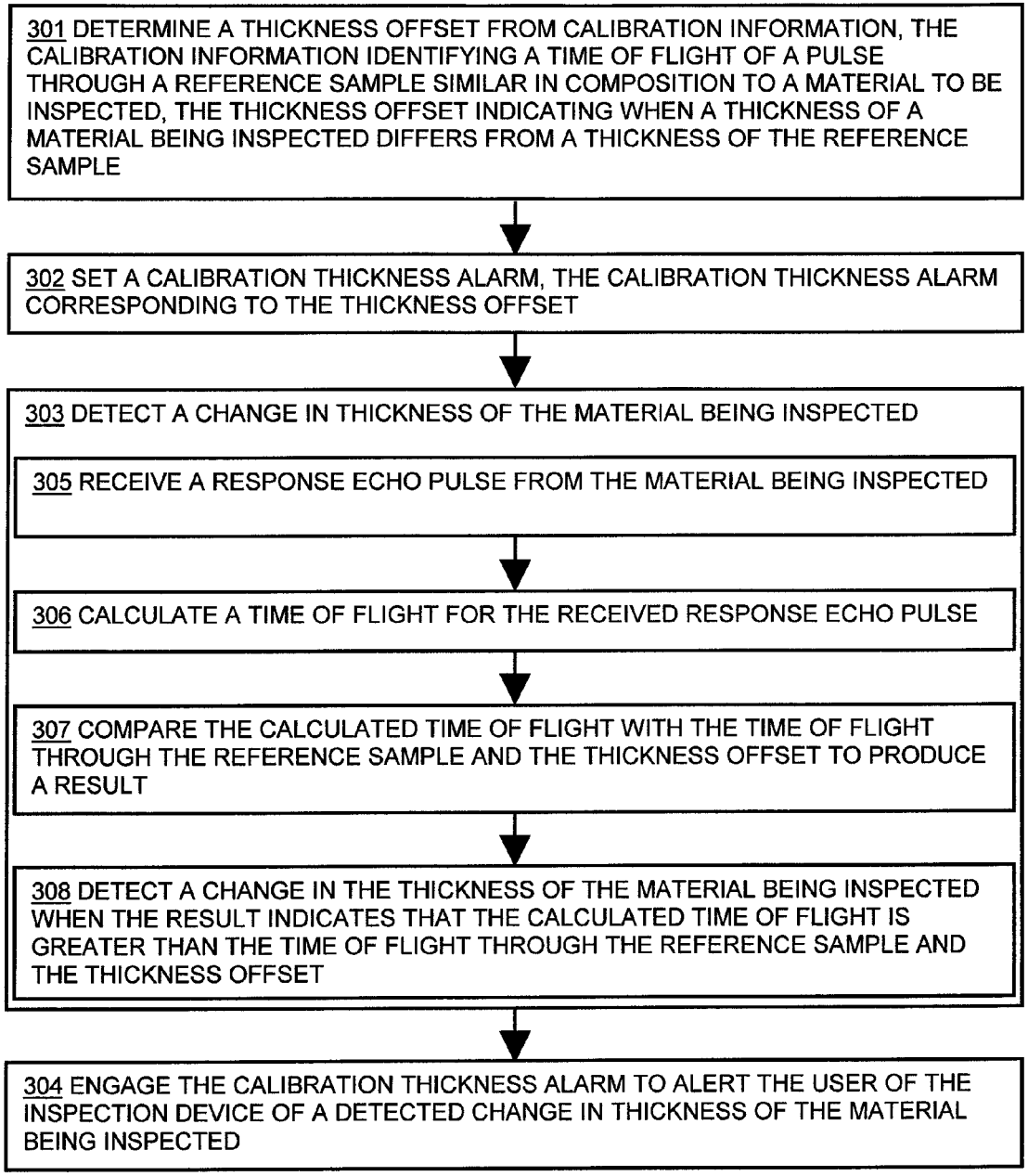
FIG. 3 illustrates a flowchart of a procedure performed by the system of FIG. 1 when alerting a user to a detection of a difference in thickness of a material being inspected.
Figure 10A:
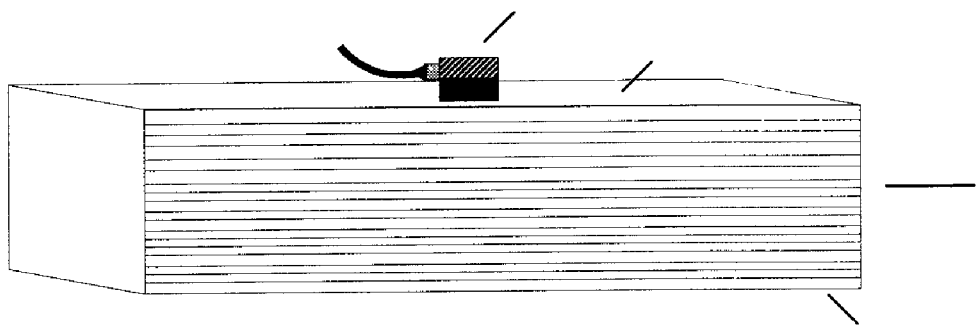
FIGS. 10A-10B illustrate an example of a material of uniform thickness with no surface marring and no subsurface damage that may be inspected using one or more transducers according to procedures described in FIGS. 3-6.
Figure 10B:
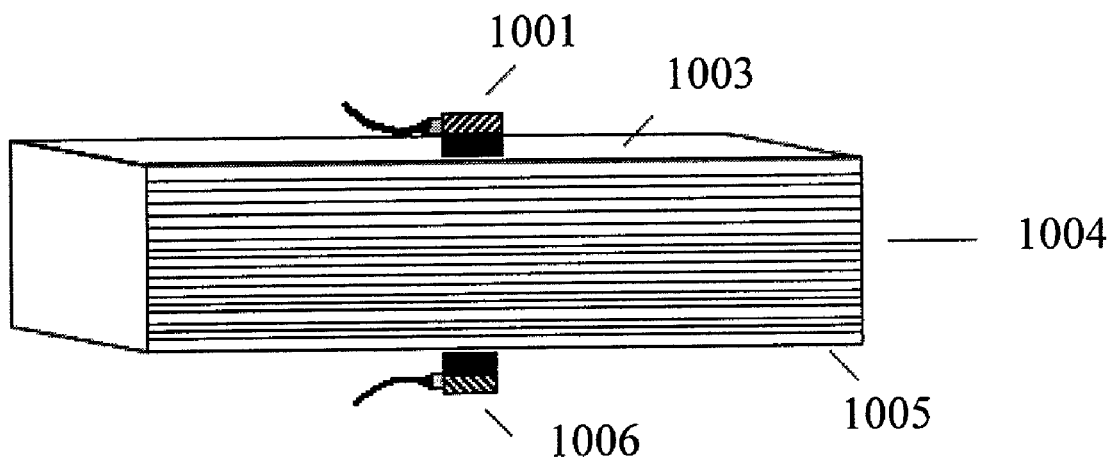

FIG. 3 illustrates the calibration thickness alarm application 140-1, executing as the calibration thickness alarm process 140-2, to alert a user (or operator) of a material inspection device of a change in thickness of a material being inspected. The calibration thickness alarm process 140-2 first determines a thickness offset from calibration information, step 301. The calibration information identifies a time of flight of a pulse through a reference sample similar in composition to a material to be inspected. Calibration information may be acquired from any number of sources. In some embodiments, a material inspection device calibrated as discussed below may transmit or otherwise transfer a copy of its stored calibration information to a non-calibrated material inspection device, for example through use of a wireless adapter in a network interface, through placing the stored calibration information on a storage medium that is provided to the non-calibrated material inspection device, or through a direct connection (i.e., a cable connected to both devices). In some embodiments, a material inspection device may receive the calibration information directly by undergoing the calibration process described below. In some embodiments, an operator of the material inspection device may provide the calibration information, for example through providing input via an input device. Note that, in some embodiments, the calibration information may be determined by measurement or calculation. A calculation of calibration information is based on the presumed velocity of the echo pulse within the material and the configuration of the measurement device transducer or transducers (e.g. "pulse-echo"or 'through-transmission' mode). Referring to FIG. 10A, the pulse-echo mode, in some embodiments, may use transducer 1001 for both pulse excitation and reception, requiring the echo pulse to travel from transducer 1001 to the back side 1005 of object 1004, and return to transducer 1001 for reception. Referring to FIG. 10b, the through-transmission mode, in some embodiments, uses transducer 1001 for pulse excitation and transducer 1006 for reception, requiring the echo pulse to travel from transducer 1001 to the back side 1005 for reception by transducer 1006. Therefore, the through-transmission time of flight will be half of what it would be for pulse-echo mode for the same object 1004.

Figure 2A:
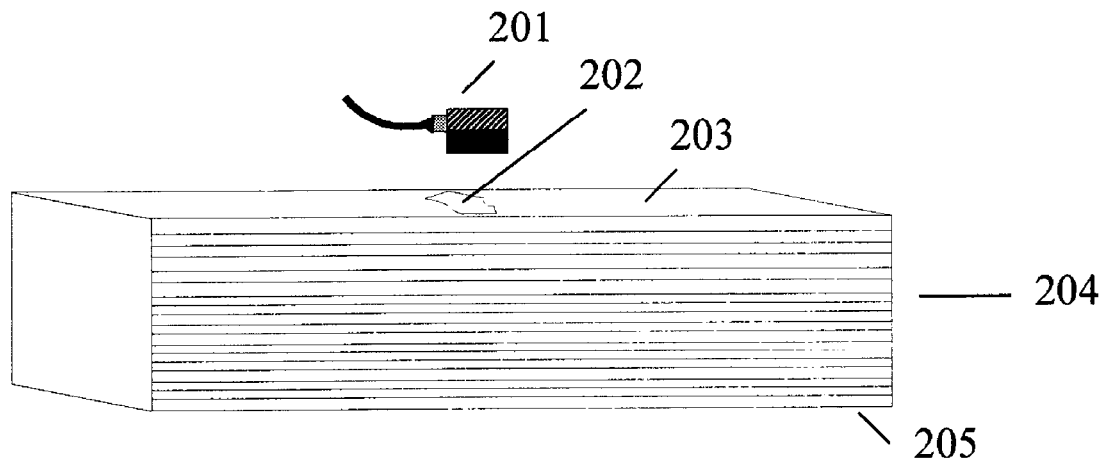
FIG. 2A illustrates an example of a material of uniform thickness with surface marring and no subsurface damage that may be inspected according to procedures described in FIGS. 3-6.
Figure 2B:
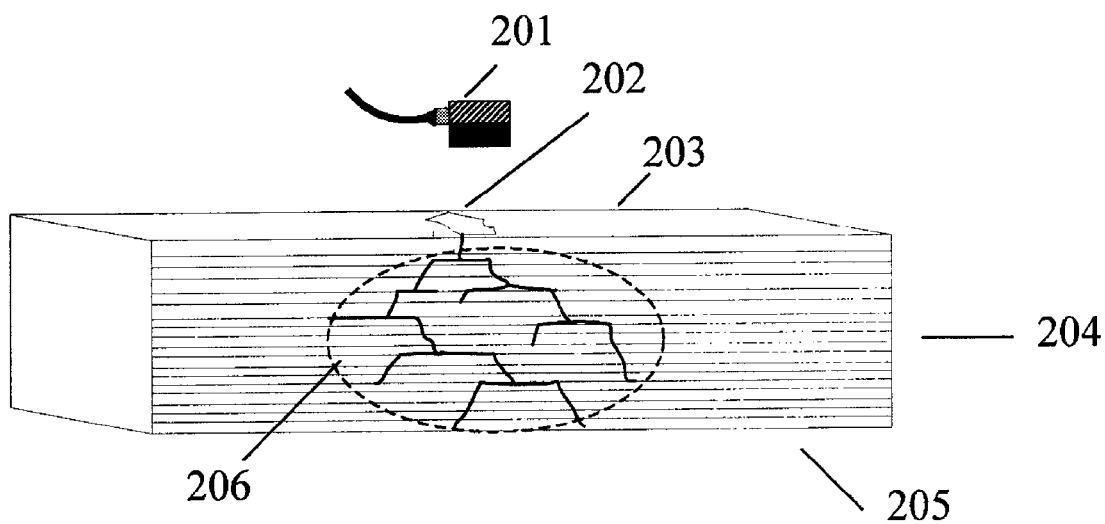
FIG. 2B illustrates an example of a material of uniform thickness with surface marring and subsurface damage that may be inspected according to procedures described in FIGS. 3-6.
Figure 2C:
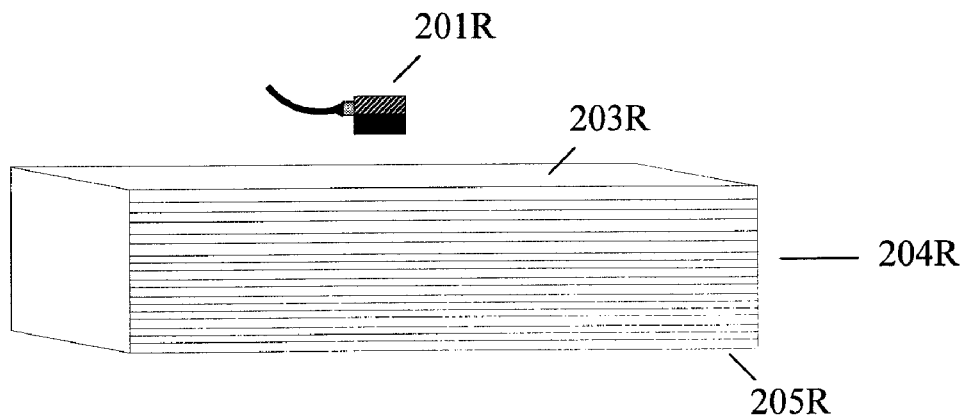
FIG. 2C illustrates an example of a material of uniform thickness with no surface marring and no subsurface damage, used during calibration according to procedures described in FIG. 36.
Figure 2D:
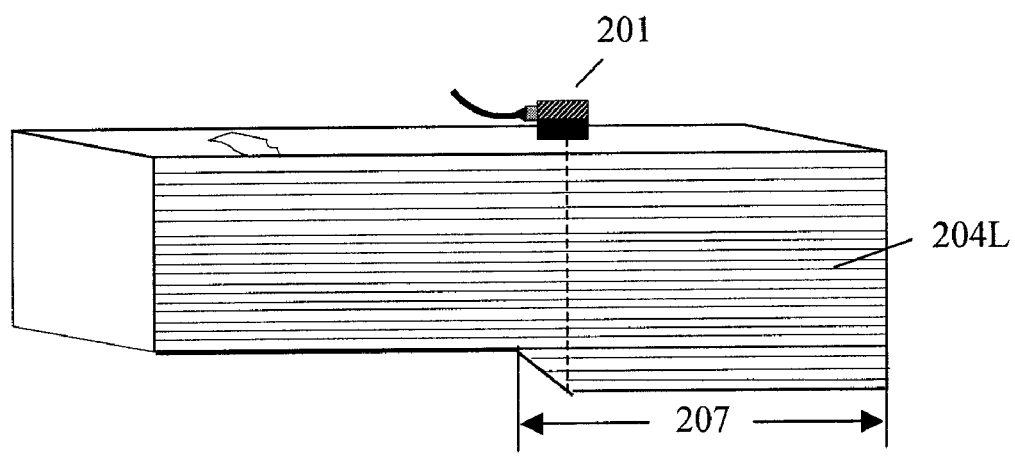
FIG. 2D illustrates an example of a material of non-uniform thickness with surface marring that is to be inspected according to procedures described in FIGS. 3-6.

Calibration information, however acquired by the calibration thickness alarm process 140-2, is created as a result of a calibration process. During the calibration process, a material inspection device, such as the material inspection device 201/201R shown throughout FIGS. 2A-2D, uses a reference sample. Note that the inspection device 201/201R, which may simply be a transducer element as described herein, may be the same device/element, and in a preferred embodiment, is the same device/element. The reference sample is similar in composition and thickness to a material to be inspected for sub-surface damage. FIGS. 2A and 2B show an example of a material 204 to be inspected by the material inspection device 201, while FIG. 2C shows an example of a reference sample 204R. The reference sample 204R has the same thickness and composition as the material 204. Note that no sub-surface damage is present in the reference sample 204R. Thus, any ultrasonic pulses the material inspection device 201R applies to the reference sample 204R will be able to travel through the reference sample 204R until they reach a rear surface 205R, at which point any pulse will be reflected back to the material inspection device 201R as a return echo pulse. The material inspection device 201R is able to use any such return echo pulse to determine the time of flight through the reference sample 204R, and thus to determine the thickness of the reference sample 204R as explained below. The material inspection device 201R determines the thickness of the reference sample 204R by using the velocity of sound through the materials, which is substantially equivalent in the material 204 and in the reference sample 204R. The material inspection device 201R determines the thickness by multiplying this velocity by the measured time of flight of an ultrasonic pulse through the reference sample 204R. The material inspection device 201R may store the thickness of the reference sample 204R, as well as the waveform of the return echo pulse, if desired, and the time of flight of the pulse, among other things, in the material inspection device 201R (e.g., in a memory unit, not shown) as calibration information.

Figure 7A:
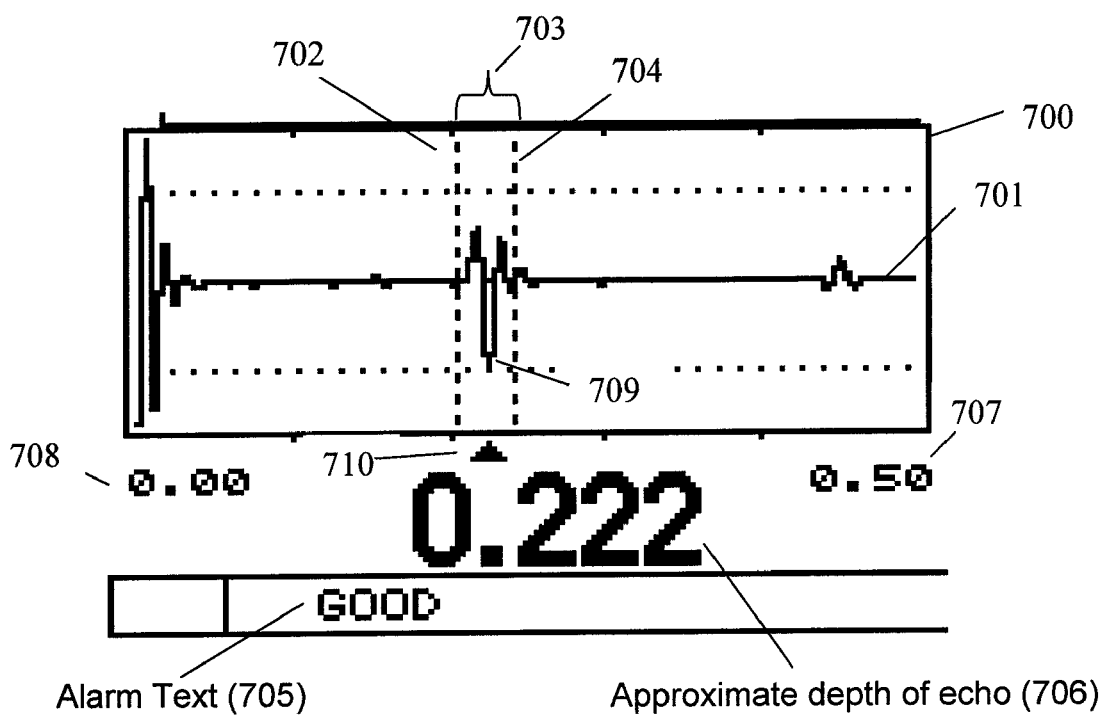
FIGS. 7A-7B illustrate example displays provided according to FIGS. 5 and 6 including a waveform of a received echo response pulse and other operational information.

Referring to FIG. 7A, when calibration information from the reference sample 204R of FIG. 2C is being used by a material inspection device 201, a return echo pulse 709 associated with the determined thickness of the reference sample 204R is indicated by a marker 710 on a display 700. The location of the marker 710 on the horizontal axis of the display 700 shown in FIG. 7A is also stored in the material inspection device 201.

The calibration thickness alarm process 140-2 uses the calibration information, obtained as described above, to determine the thickness offset. The thickness offset indicates when a thickness of a material being inspected differs from a thickness of the reference sample. The thickness offset may be determined in any number of ways. For example, referring again to FIG. 7A, the location, in time, of the return echo pulse 709 used during calibration may be used to determine the thickness offset. In some embodiments, the calibration thickness alarm process 140-2 may determine a thickness offset by receiving the offset as input from an operator, or by selecting from among default offsets accessible to the calibration thickness alarm process 140-2, or by employing any other calibration methods known in the art.

The calibration thickness alarm process 140-2 then sets a calibration thickness alarm, step 302. Examples of calibration thickness alarms are discussed in greater detail below. The calibration thickness alarm corresponds to the thickness offset. For example, referring again to FIG. 7A, the calibration thickness alarm process 140-2 may use the thickness offset to measure a point in time from a location in time on the return echo pulse 709 (identified by the marker 710) and that point is a calibration thickness alarm point (shown by a marker 704 in FIG. 7A). Whenever a time of flight of a pulse the material inspection device transmits through a material being inspected is greater (in terms of time) than the time indicated by the calibration thickness alarm point, the calibration thickness alarm will be engaged.

With the calibration thickness alarm set, an operator is able to use the material inspection device to inspect material of substantially the same thickness as the reference sample used to create the calibration information used by the calibration thickness alarm process 140-2. During such inspections, the operator will cause the material inspection device to emit one or more ultrasonic pulses through the material being inspected at different locations on the surface of the material. Should the operator move the material inspection device to a location where the thickness of the underlying material is different from the thickness of the reference sample, the calibration thickness alarm process 140-2 detects such a change in thickness of the material being inspected, step 303. For example, referring to FIGS. 2B and 2D, the calibration thickness alarm process 140-2 will detect no change in thickness in the material 204 shown in FIG. 2B. That is, a time of flight of any pulse transmitted by the material inspection device through the material 204 shown in FIG. 2B is going to return in less time, or in (substantially) equivalent time, in comparison to the time identified by the calibration thickness alarm point. In other words, a pulse transmitted through the material 204 shown in FIG. 2B is going to either encounter damage 206, and return in less time, or the rear surface 205, and return in (substantially) equivalent time. In contrast, in FIG. 2D, if an operator places the material inspection device 201 on a portion 207 of a material 204L, the calibration thickness alarm process 140-2 will detect a change in thickness. A time of flight for a pulse transmitted by the material inspection device 201 through the portion 207 is going to take longer to reach the rear surface of the material 204L because that portion 207 has a greater thickness than the reference sample 204R.

Finally, the calibration thickness alarm process 140-2 engages the calibration thickness alarm to alert the user (i.e., operator) of the inspection device of a detected change in thickness of the material being inspected, step 304. The calibration thickness alarm process 140-2 may, for example, present the alarm via a graphical user interface, as described below with regards to FIG. 5. In some embodiments, the calibration thickness alarm process 140-2 engages the alarm through use of some combination of other visual, audio, or vibratory forms of alarm. For example, the calibration thickness alarm process 140-2 may emit a beeping noise, or may vibrate in the operator's hand, or a combination thereof.

In some embodiments, the calibration thickness alarm process 140-2 detects a change in thickness according to the following procedure. The calibration thickness alarm process 140-2 receives a response echo pulse from the material being inspected, step 305. Thus, the material inspection device transmits an ultrasonic pulse through the material being inspected, and that pulse is reflected off of something within the material, either damage or a rear surface. The calibration thickness alarm process 140-2 then calculates a time of flight for the received response echo pulse, step 306. The time of flight is simply the amount of time the pulse needed to travel and then return through the material. The calibration thickness alarm process 140-2 compares the calculated time of flight with the time of flight through the reference sample and the thickness offset to produce a result, step 307. The result indicates whether the time of flight for the received response echo pulse is greater than the time of flight from the calibration information, or less. The calibration thickness alarm process 140-2 then uses the result to detect a change in thickness. That is, the calibration thickness alarm process 140-2 detects a change in the thickness of the material being inspected when the result indicates that the calculated time of flight is greater than the time of flight through the reference sample and the thickness offset, step 308. Again referring to FIG. 2D, the time of flight of a pulse through the portion 207 of the material 204L is going to be greater than the time of flight of a pulse through the reference sample 204R, which indicates a change in thickness in comparison to the thickness of the reference sample 204R.

Figure 2E:
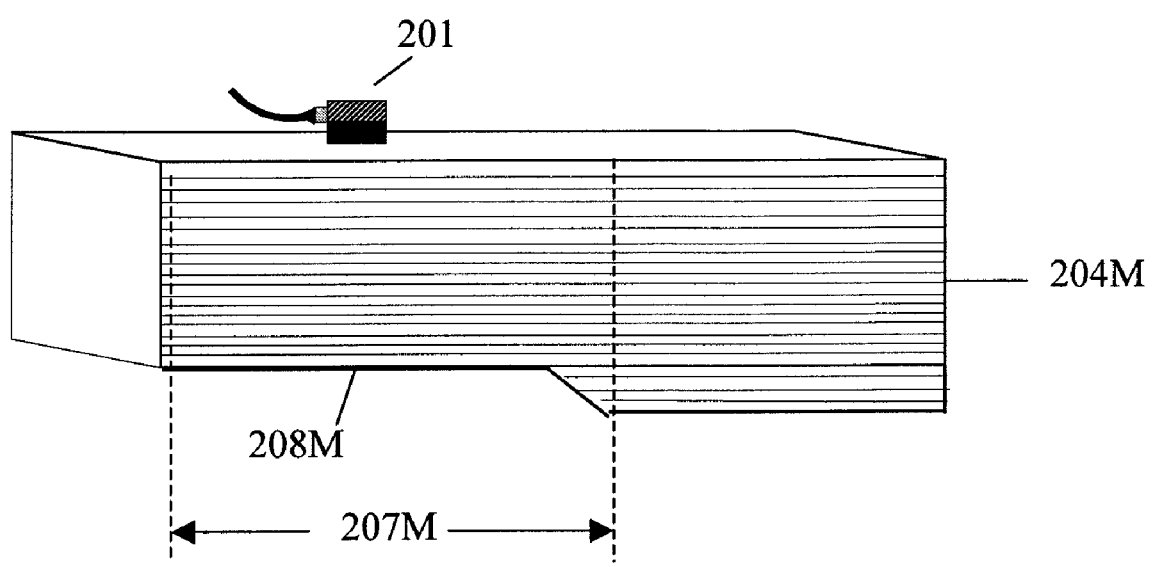
FIG. 2E illustrates an example of a material of non-uniform thickness with surface marring that is to be inspected according to procedures described in FIGS. 3-6.

Note that, in some embodiments, a material inspection device may be able to determine when a material or other object being inspected is thinner than a reference sample. For example, as shown in FIG. 2E, when an operator places transducer 201 over portion 207M of a material 204M, the calibration thickness alarm process 140-2 will detect a change in thickness. A time of flight for a pulse transmitted by the transducer 201 through the portion 207M is going to take less time to reach the rear surface of the material 204M because that portion 207 has a thickness that is less than the reference sample 204R. Furthermore, the amplitude of response echo 709B will be substantially the same as that of 709 obtained through calibration thickness alarm process 140-2, thereby allowing it to be distinguished from an echo response caused by reflection from sub-surface damage.

When these conditions are met, an alarm indication for the 'Beneath Cal Thickness' (not shown) will be caused. As with the other embodiments, different methods of alarm indication may be used, such as, but not limited to graphical, LED, audio and vibratory.

Figure 7B:
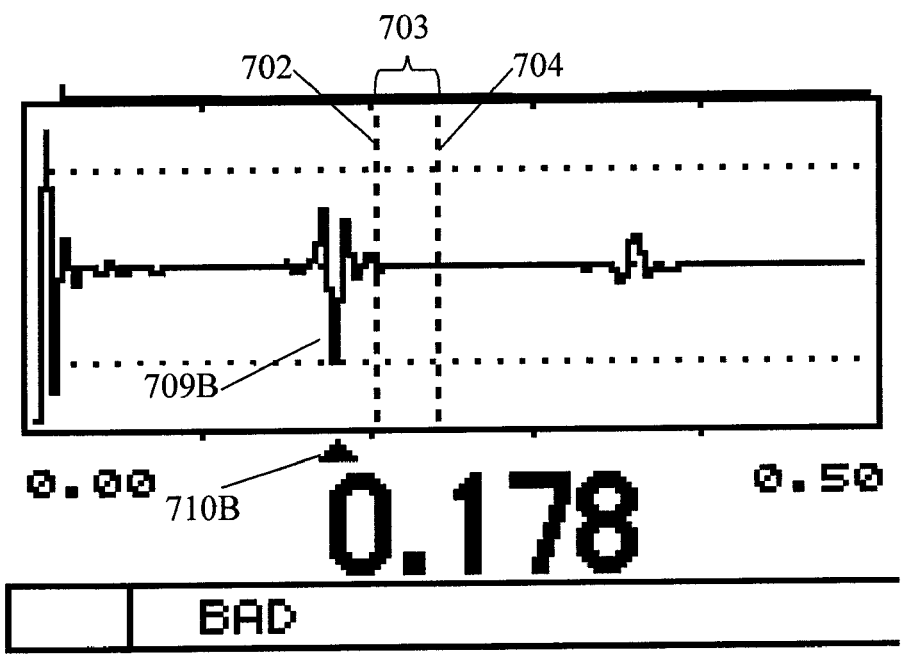

Referring to FIG. 7B, because echo 709B occurs to the left of damage alarm point 702, it can be caused by either a 'Beneath Cal Thickness' or 'Damage Detection' alarm condition. Because of this, thickness alarm process 140-2 must be able to distinguish between an echo response caused by damage within the material, such as 206, and an echo response caused by reflecting from thinner region 207M.

In order to achieve this, the amplitude of calibrated response echo 709 must be compared to the amplitude of echo 709B. The amplitude of echo 709B when caused by refection from back wall surface 208M will be substantially greater than if echo 709B was caused by reflection from sub-surface damage. It is worth noting that the large amplitude response of a back wall echo is caused by a significant acoustic impedance mismatch between back wall 208M and the adjacent air, which is not typically the case for sub-surface damage. Differences in acoustic impedance in the region of sub-surface damage 206 are substantially smaller than that of the back wall surface 208M and the adjacent air.

The amplitude of the response echoes may be determined in several ways. A preferred embodiment uses an automatic gain control technique (AGC) to maintain the response echoes, such as 709 and 709B, close to predetermined set point (e.g. 75% of the device's full scale range). The gain setting of the AGC is stored in memory for use to compare amplitudes in thickness alarm process 140-2. Other methods for determining response echo amplitude may be accomplished by direct measurement of the echo peaks, or signal slew rates.

In FIG. 4, the calibration thickness alarm process 140-2 determines a thickness offset using a different procedure than described in FIG. 3 above. The calibration thickness alarm process 140-2 determines a thickness offset, step 401, by first determining a damage offset from calibration information, step 405. The calibration information identifies a time of flight of a pulse through a reference sample similar in composition to a material to be inspected, as described above. The damage offset identifies a point in time at which, if a received echo pulse has a time of flight shorter than the identified point in time, damage is likely present in the material being inspected. In other words, the damage offset is the location on the time of flight path that indicates the maximum thickness of the material where a valid damage indication may occur. For example, in the material 204 shown in FIG. 2B, damage 206 will cause an ultrasonic pulse from a material inspection device 201 to reflect such that its time of flight will be less the time of flight of a pulse reflected in the reference sample 204R or a material 204 containing no damage (as shown in FIG. 2A, for example). As with a thickness offset, a damage offset may, in some embodiments, be determined: through analysis performed by the calibration thickness alarm process 140-2, by selection of one of a number of default setting, by operator selection or input, or by any other known calibration methods. The damage offset is then used to set a damage alarm point 402 (shown in FIG. 7A), such as by, for example, subtracting the damage offset (which may, in some embodiments, be a fixed value) from the calibrated thickness of the reference sample identified by marker 410.

The calibration thickness alarm process 140-2 then determines the thickness offset from the damage offset, step 406, the thickness offset indicating when a thickness of a material being inspected differs from a thickness of the reference sample. In other words, referring to FIG. 7A, the calibration thickness alarm process 140-2 may determine the thickness offset by adding the amount of time between a location on the pulse 709 (indicated by the marker 710) and the damage point (indicated by the marker 702) (i.e., the damage offset) to the time indicated by the location on the pulse 709 by the marker 710. This establishes a range 703 in which, if a return echo pulse falls within this range, no damage is considered present in the material being inspected and the thickness of the material has not changed. Note that, in some embodiments, the determination of the thickness offset by the calibration thickness alarm process 140-2 may use an amount of time that is different than amount of time between a location in time in relation to the pulse 709 (indicated by the marker 710) and the damage point (indicated by the marker 702). That is, the difference in time between the marker 710 and the marker 702 may differ from the difference in time between the marker 710 and the marker 704.

The calibration thickness alarm process 140-2 then sets a calibration thickness alarm corresponding to the thickness offset, step 402; detects a change in thickness of the material being inspected, step 403, and engages the calibration thickness alarm to alert the user (i.e., operator) of the inspection device of a detected change in thickness of the material being inspected, step 404, all as described herein. In some embodiments, the calibration thickness alarm process 140-2 may detect a change by first receiving a response echo pulse from the material being inspected, step 405. The calibration thickness alarm process 140-2 then calculates a time of flight for the received response echo pulse, step 406, and compares the calculated time of flight with the damage offset and the thickness offset to produce a result, step 407. This comparison may use the range 703 described above. That is, if the calculated time of flight is not less than the damage alarm point 702 and is not more than the calibration thickness alarm point 704, then the received response echo pulse does not show damage in the material being inspected, and the material is of the appropriate thickness. Alternatively, if the calculated time of flight is less than the damage alarm point 702, then damage is likely present. If the calculated time of flight is greater than the calibration thickness alarm point 704, then the calibration thickness alarm process 140-2 uses this result to detect a change in the thickness of the material being inspected, step 408.

Figure 5:
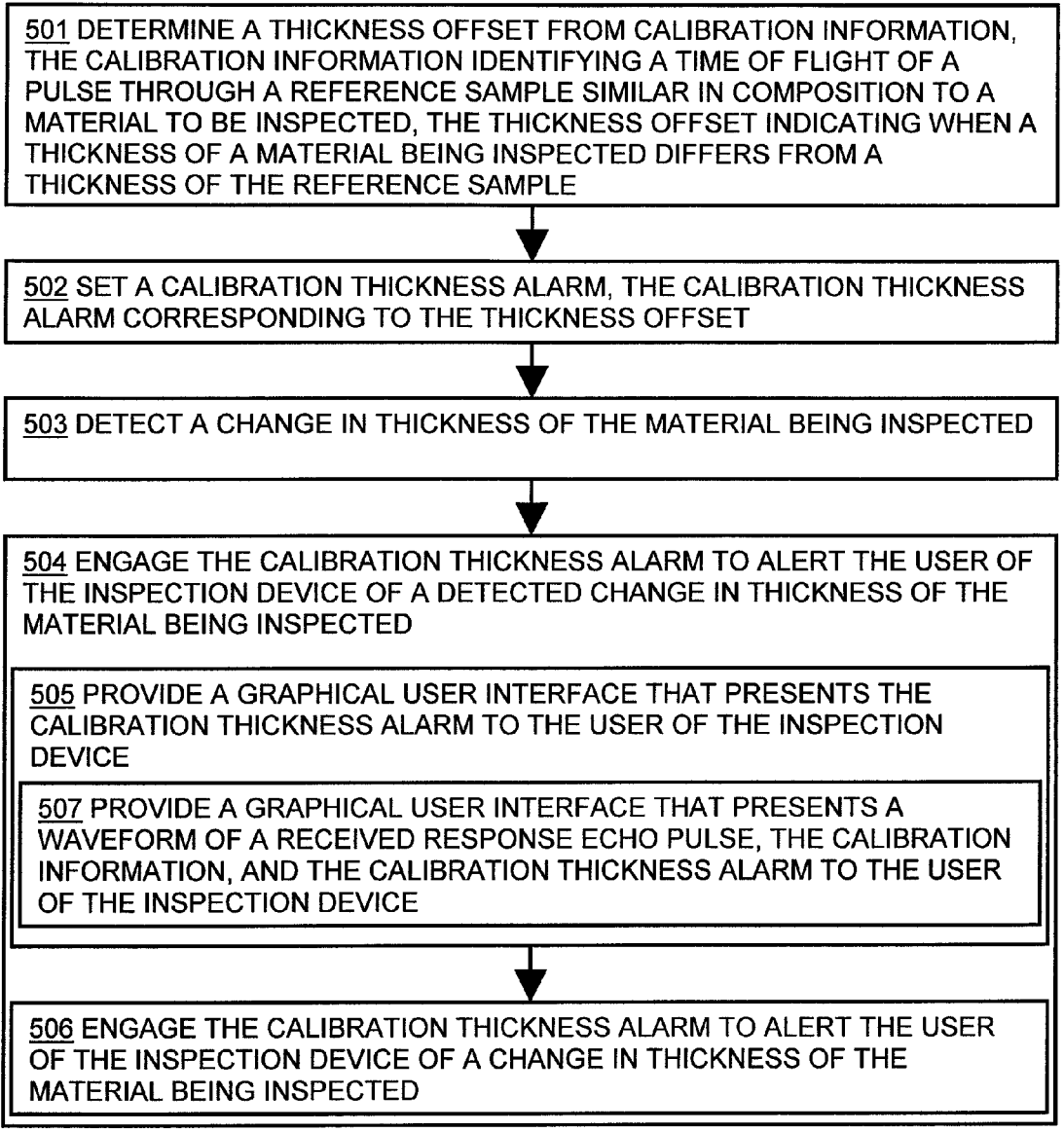
FIG. 5 illustrates a flowchart of a procedure performed by the system of FIG. 1 when presenting the alert of a detection of a difference in thickness of a material being tested via a graphical user interface.

FIG. 5 illustrates the calibration thickness alarm process 140-2 providing a graphical user interface through which a calibration thickness alarm is presented to an operator of a material inspection device. The calibration thickness alarm process 140-2 determines a thickness offset from calibration information, step 501. The calibration information identifies a time of flight of a pulse through a reference sample similar in composition to a material to be inspected. The thickness offset indicates when a thickness of a material being inspected differs from a thickness of the reference sample. The calibration thickness alarm process 140-2 then sets a calibration thickness alarm, step 502. The calibration thickness alarm corresponds to the thickness offset. The calibration thickness alarm process 140-2 detects such a change in thickness of the material being inspected, step 503. These steps are performed as described above with regards to FIGS. 3 and 4. Finally, the calibration thickness alarm process 140-2 engages the calibration thickness alarm to alert the user (i.e., operator) of the inspection device of a detected change in thickness of the material being inspected, step 504.

Here, the calibration thickness alarm process 140-2, when engaging, provides a graphical user interface that presents the calibration thickness alarm to the user of the inspection device, step 505, and then engages the calibration thickness alarm to alert the user of the inspection device of a change in thickness of the material being inspected, step 506. In some embodiments, the calibration thickness alarm process 140-2 provides a graphical user interface that presents a waveform of a received response echo pulse, the calibration information, and the calibration thickness alarm to the user of the inspection device, step 507.

Thus, referring to FIGS. 7A and 7B, a skilled operator of a material inspection device may derive a significant amount of useful information by observing a graphical representation of a waveform of a pulse that the calibration thickness alarm process 140-2 may present on a graphical user interface (shown on the display 400). Such a graphical representation of the waveform of the pulse may provide a visual representation of ultrasonic signal events occurring within the material being inspected that are pertinent to both proper measurement setup and the damage detection process. For example, in the case of waveform 701, the appearance of the waveform indicates that the measurement setup is correct because echo 709 is of sufficient amplitude and properly positioned. Note that, although noise is shown in FIG. 7A, echo 709 may coexist with noise from sources such as multipath echoes, susceptibility to external noise sources, and self-generated electronic system noise. A good signal-to-noise ratio is advantageous in terms of signal processing performance, such as is performed by the material inspection device, as that results in a higher confidence level in the inspection measurements taken by the material inspection device. Presenting a graphical representation of a waveform of a pulse 709 also allows an operator of the material inspection device to know if errors are present. For example, if a pulse 709 did not appear on display 700, the operator would know a problem exists, perhaps due to calibration information error or improper coupling of the material inspection device to the material being inspected.

As shown in FIG. 7A, graphic character information fields 705, 706, 707, and 708 may each provide useful information to the operator of the material inspection device about alarm status, approximate depth of echo, and starting depth and ending depth of displayed signal range, respectively. An alarm status text field 705 indicates, for example, whether the material inspection device detects no damage (i.e., GOOD), damage (i.e., BAD), or if the thickness of the material being measured is different from a thickness of a reference sample used to calibrate the material inspection device (i.e., BEYOND CAL THICKNESS), all as described above. Each status indicator provides an operator with the advantage of knowing, in real time, the particular status of an alarm condition when the operator is viewing the display 700.

An approximate depth of damage indicator 706 provides a numeric estimate of the depth of a section of subsurface damage 206, shown in FIG. 2B, within the material 204 being inspected. As described herein, the material inspection device/calibration thickness alarm process 140-2 measures the time of flight of an echo pulse within the material, which is then converted to depth by applying a time of flight to thickness conversion transfer function that may be determined during calibration.

An ending depth indicator 707 and a starting depth indicator 708, in total, indicate the range of depth within the material shown on the display 700. This allows an operator to obtain a quick visual assessment of the depth of any damage within the material being inspected, or how far an echo pulse is beyond the valid calibration thickness. The ending depth indicator 707 is set through calibration information that is a result of the calibration process, or user input (e.g. a previously known or calculated value), and may, in some embodiments, include an additional offset distance. The starting depth indicator 708 is determined upon placement of the material inspection device on the material to be inspected and transmission of a pulse there through. The starting depth indicator 708 and ending depth indicator 707 may also be determined by user input.

In FIG. 6, the calibration thickness alarm process 140-2 provides a graphical user interface for purposes other than alerting a user to a change in thickness of a material being tested. The calibration thickness alarm process 140-2 determines a thickness offset from calibration information, step 601. The calibration information identifies a time of flight of a pulse through a reference sample similar in composition to a material to be inspected. The thickness offset indicates when a thickness of a material being inspected differs from a thickness of the reference sample. The calibration thickness alarm process 140-2 then sets a calibration thickness alarm, step 602. The calibration thickness alarm corresponds to the thickness offset. The calibration thickness alarm process 140-2 then detects such a change in thickness of the material being inspected, step 603, and engages the calibration thickness alarm to alert the user (i.e., operator) of the inspection device of a detected change in thickness of the material being inspected, step 604. Here, prior to detecting, the calibration thickness alarm process 140-2 provides a graphical user interface to the user, step 605. The graphical user interface is capable of presenting a received response echo pulse and information concerning the material being inspected.

Figure 8A:
FIGS. 8A-8H illustrate example displays of a material inspection device.
Figure 8B:
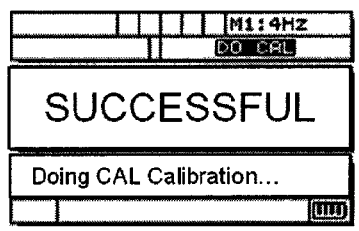
Figure 8C:
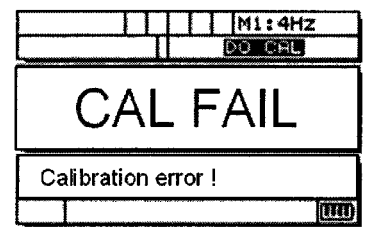
Figure 8D:
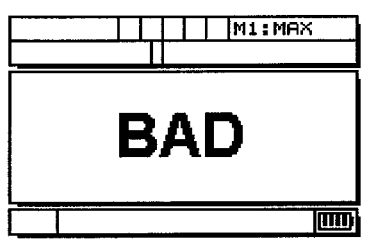
Figure 8E:
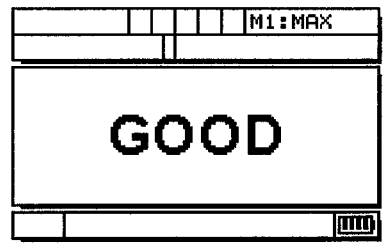
Figure 8F:
Figure 8G:
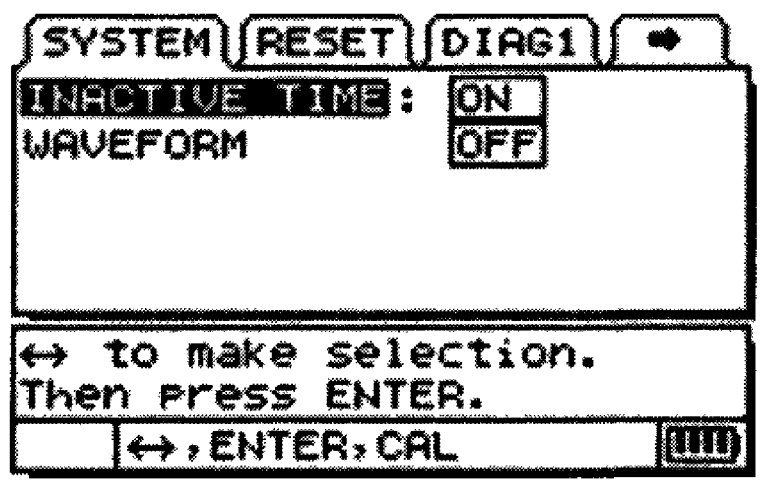
Figure 8H:
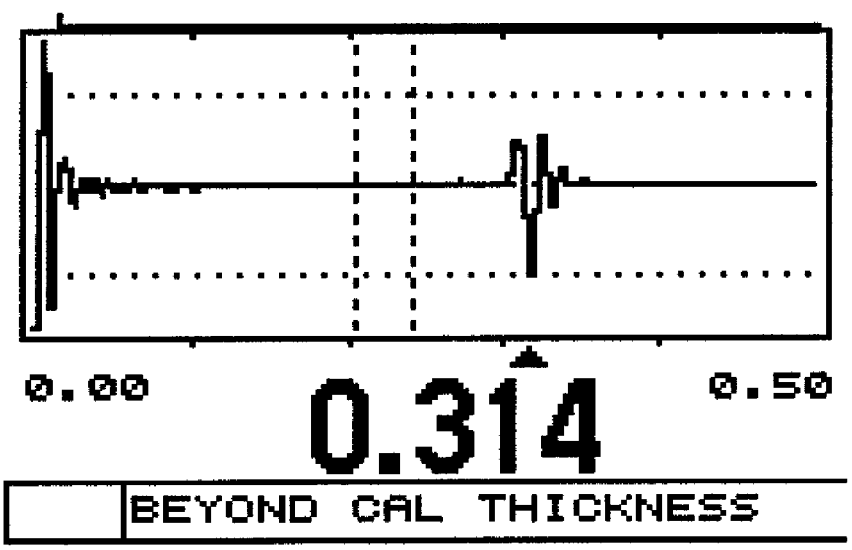

In other words, the graphical user interface provided by the calibration thickness alarm process 140-2 need not be used to present the calibration alarm, but rather, in some embodiments, may simply be used to display the waveform of a response echo pulse, as well as other information, to a user. For example, the graphical user interface provided by the calibration thickness alarm process 140-2 may, in some embodiments, give an operator step-by-step instructions to help ensure proper calibration, as shown in FIGS. 8A and 8G. Examples of these instructions and their results may be seen in FIGS. 7B and 8F. In some embodiments, the graphical user interface provided by the calibration thickness alarm process 140-2 may provide various commands through a command menu structure such as is shown in FIG. 8G. For example, an operator may select settings using the SYSTEM tab, may reset the system using the RESET tab, and may view diagnostic information using the DIAG tabs. Although not shown in FIG. 8G, such a graphical user interface may also include one or more PARAMETERS tab(s) that allow the operator to set any and all available device parameters, including but not limited to gain.

As discussed above with regards to FIGS. 3-5, the graphical user interface provided by the calibration thickness alarm process 140-2 may show a waveform 701 with alarm markers 702 and 704, center of return echo pulse marker 710, an approximate depth of echo 706, and an alarm condition 705. Such information may be useful to an operator in determining the quality of the measurement being made by the material inspection device, as well as providing any alarm indications. In some embodiments, the graphical user interface may include an indicator, for example in the lower right-hand corner, for remaining battery capacity, which enables the operator to know how the remaining capacity of the battery.

Such an indicator is shown in FIGS. 8A-8G. As described above with regards to FIGS. 3 and 5, the calibration thickness alarm process 140-2 may use other visual, audio, vibratory, or any other forms of indication for alarms and the like in addition to, or in place of, the graphical user interface.

In some embodiments, the calibration thickness alarm process 140-2 may not display a received pulse well due to the amplitude of the pulse being small in comparison to the measurement range of the material inspection device and/or the display (i.e., the graphical user interface). Thus, the calibration thickness alarm process 140-2 may use an automatic gain control; that is, the calibration thickness alarm process 140-2 may automatically amplify amplitude of the received response echo pulse to optimize the received response echo pulse in regards to a range of the inspection device shown on the graphical user interface, step 606. An automatic gain control ensures that the received echo signal is amplified to meet an optimal level within the full-scale range of the material inspection device (e.g., 75% of the full scale range). This ensures that a substantially optimal signal to noise ratio is consistently maintained throughout use of the material inspection device on the material being inspected. In some embodiments, a successive approximation method is used for the automatic gain control; however, other methods may also be used.

In some embodiments, the calibration thickness alarm process 140-2 may instead use a time-varied gain control. That is, the calibration thickness alarm process 140-2 automatically applies a time-varied gain to a first received response echo pulse and a second received response echo pulse to optimize the first received response echo pulse and the second received response echo pulse in regards to a range of the inspection device shown on the graphical user interface, step 607.

A time-varied gain may compensate for echo pulse attenuation as the pulse travels through the material, by applying an inverse amplitude curve that ensures that the echo amplitude is substantially constant regardless of its position along the time of flight path. The time-varied gain control thus helps to ensure that the amplitude of an echo pulse is substantially optimized for the full-scale range of the material inspection device, regardless of the position of the pulse along the time of flight path. Alternatively, a time-varied gain control may compensate for high dynamic range echo events. For example, damage detection near a rear surface 205 of material 204 (shown in FIG. 2B, for example) is often limited by the large amplitude response of the echo pulse from the rear surface 205.

Figure 9:
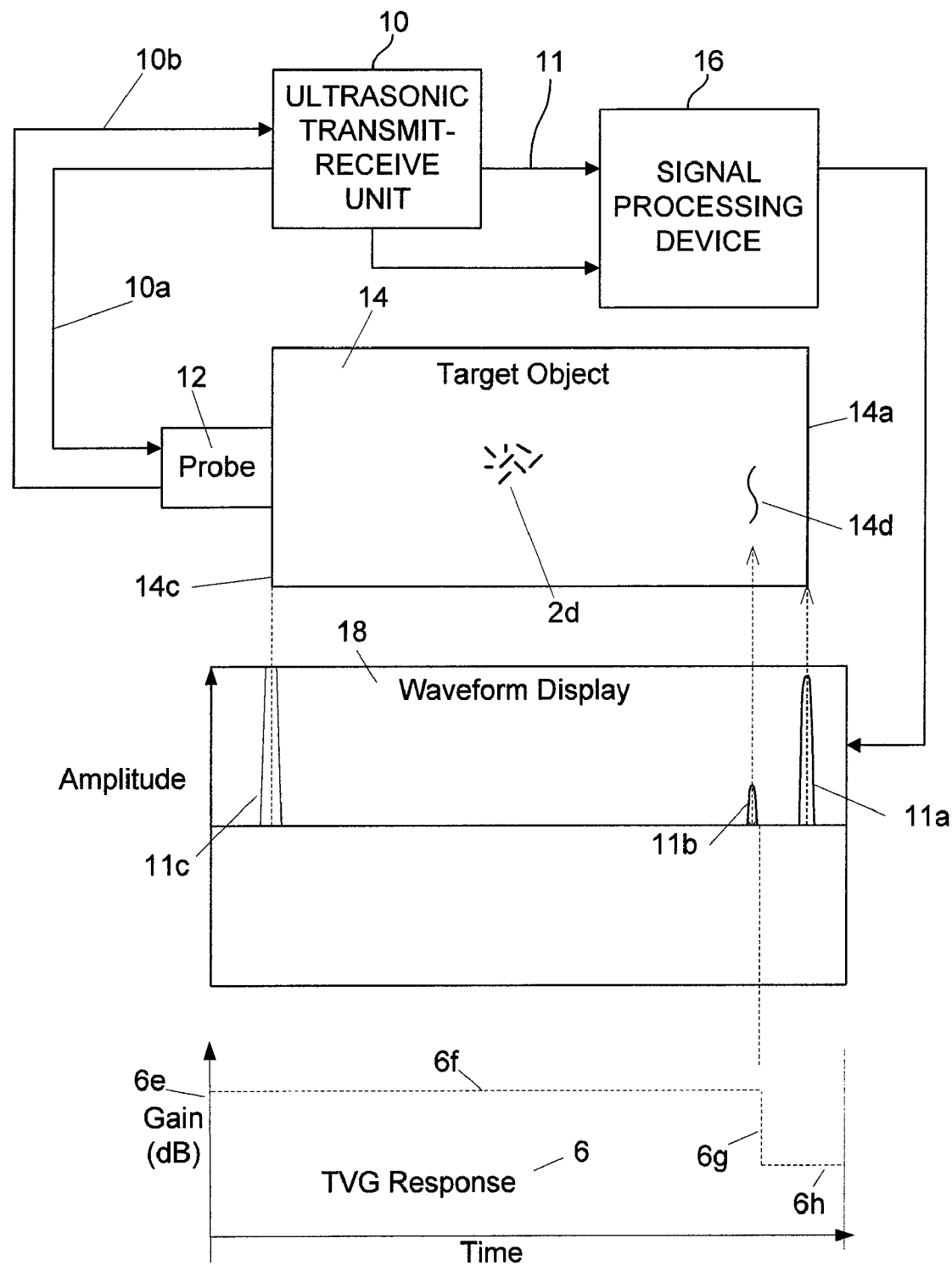
FIG. 9 is a block diagram that provides an example side-by-side comparison of a waveform displayed on a material inspecting device with damage locations in a material being tested.

Referring to FIG. 9, damage 14d is very close to rear surface 14a which results in echoes 11b and 11a, respectively. The echo amplitude of the echo 11a will be much greater than the amplitude of echo 11b. The calibration thickness alarm process 140-2 cannot display echo 11a within the full-scale displayed range (i.e., unclipped) on the same display 18 with constant gain and a linear vertical gain scale. To solve this, the calibration thickness alarm process 140-2 applies a time-varied gain curve such as shown in FIG. 9. The curve comprises 6f, 6g and 6h. The calibration thickness alarm process 140-2 applies this curve to achieve the viewable echo amplitudes of 11b and 11a, both of which are not clipped and are thus clearly visible on the display 18. Note that it is important to view echo 11a with its peak appearing because differences in its amplitude during inspection may be indicative of poor coupling of the material inspection device to the material being inspected, or of attenuating affects of irregularities within the material being inspected.

In some embodiments, reflections from side surfaces of a material may return to the material inspection device prior to the echo reflection from a calibrated rear surface (i.e., 205R shown in FIG. 2C). This may cause a false damage alarm if not properly compensated for. In such situations, the time-varied gain curve of FIG. 9 may be adjusted to compensate for false alarm echoes (not shown) by reducing the gain at the location of the false echo as long as its position along the time of flight path is substantially constant.

In related embodiments, a false damage alarm may result in a similar way when substantial acoustic impedance inconsistencies exist within the material being inspected. For example, two materials of substantially different material composition may be bonded together. This may cause a false damage echo to occur to the left of the damage alarm point 702 shown in FIG. 7A. The time-varied gain curve of FIG. 9, 6f, 6g and 6h may be adjusted to compensate for this false damage echo (not shown) as well by reducing the gain at the location of the false damage echo as long as its position along the time of flight path is substantially constant.

The methods and systems described herein are not limited to a particular hardware or software configuration, and may find applicability in many computing or processing environments. The methods and systems may be implemented in hardware or software, or a combination of hardware and software. The methods and systems may be implemented in one or more computer programs, where a computer program may be understood to include one or more processor executable instructions. The computer program(s) may execute on one or more programmable processors, and may be stored on one or more storage medium readable by the processor (including volatile and non-volatile memory and/or storage elements), one or more input devices, and/or one or more output devices. The processor thus may access one or more input devices to obtain input data, and may access one or more output devices to communicate output data. The input and/or output devices may include one or more of the following: Random Access Memory (RAM), Redundant Array of Independent Disks (RAID), floppy drive, CD, DVD, magnetic disk, internal hard drive, external hard drive, memory stick, flash memory (i.e., solid state memory) device, or other storage device capable of being accessed by a processor as provided herein, where such aforementioned examples are not exhaustive, and are for illustration and not limitation.

The computer program(s) may be implemented using one or more high level procedural or object-oriented programming languages to communicate with a computer system; however, the program(s) may be implemented in assembly or machine language, if desired. The language may be compiled or interpreted.

As provided herein, the processor(s) may thus be embedded in one or more devices that may be operated independently or together in a networked environment, where the network may include, for example, a Local Area Network (LAN), wide area network (WAN), and/or may include an intranet and/or the Internet and/or another network. The network(s) may be wired or wireless or a combination thereof and may use one or more communications protocols to facilitate communications between the different processors. The processors may be configured for distributed processing and may utilize, in some embodiments, a client-server model as needed. Accordingly, the methods and systems may utilize multiple processors and/or processor devices, and the processor instructions may be divided amongst such single- or multiple-processor/devices.

The device(s) or computer systems that integrate with the processor(s) may include, for example, a personal computer (s), workstation(s) (e.g., Sun, HP), personal digital assistant (s) (PDA(s)), handheld device(s) such as cellular telephone (s), laptop(s), handheld computer(s), or another device(s) capable of being integrated with a processor(s) that may operate as provided herein. Accordingly, the devices provided herein are not exhaustive and are provided for illustration and not limitation.

References to "a microprocessor" and "a processor", or "the microprocessor" and "the processor," may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor" or "processor" terminology may thus also be understood to include a central processing unit, an arithmetic logic unit, an application-specific integrated circuit (IC), and/or a task engine, with such examples provided for illustration and not limitation.

Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where such memory may be contiguous and/or partitioned based on the application. Accordingly, references to a database may be understood to include one or more memory associations, where such references may include commercially available database products (e.g., SQL, Informix, Oracle) and also proprietary databases, and may also include other structures for associating memory such as links, queues, graphs, trees, with such structures provided for illustration and not limitation.

References to a network, unless provided otherwise, may include one or more intranets and/or the Internet. References herein to microprocessor instructions or microprocessor-executable instructions, in accordance with the above, may be understood to include programmable hardware.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun may be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Those skilled in the art may make many additional changes in the details, materials, and arrangement of parts, herein described and illustrated.

What is claimed is:

1. A method of alerting a user of a material inspection device of a change in thickness of a material being inspected, the method comprising:

determining a thickness offset from calibration information, the calibration information identifying a time of flight of a pulse through a reference sample similar in composition to a material to be inspected, the thickness offset indicating when a thickness of a material being inspected differs from a thickness of the reference sample;

setting a calibration thickness alarm, the calibration thickness alarm corresponding to the thickness offset;

detecting a change in thickness of the material being inspected;

engaging the calibration thickness alarm to alert the user of the inspection device of a detected change in thickness of the material being inspected, determining a damage offset from calibration information, the calibration information identifying a time of flight of a pulse through a reference sample similar in composition to a material to be inspected; and determining a thickness offset from the damage offset, the thickness offset indicating when a thickness of a material being inspected differs from a thickness of the reference sample.

2. The method of claim 1 wherein detecting comprises:

receiving a response echo pulse from the material being inspected;

calculating a time of flight for the received response echo pulse;

comparing the calculated time of flight with the damage offset and the thickness offset to produce a result; and detecting a change in the thickness of the material being inspected when the result indicates that the calculated time of flight is greater than the damage offset and the thickness offset.

3. The method of claim 1 wherein engaging comprises:

providing a graphical user interface that presents the calibration thickness alarm to the user of the inspection device; and engaging the calibration thickness alarm to alert the user of the inspection device of a change in thickness of the material being inspected.

4. The method of claim 1 further comprising:

providing a graphical user interface that presents a waveform of a received response echo pulse, the calibration information, and the calibration thickness alarm to the user of the inspection device.

5. The method of claim 1 comprising:

providing a graphical user interface to the user, the graphical user interface capable of presenting a received response echo pulse and information concerning the material being inspected.

6. The method of claim 5 comprising:

automatically amplifying an amplitude of the received response echo pulse to optimize the received response echo pulse in regards to a range of the inspection device shown on the graphical user interface.

7. The method of claim 5 comprising:

automatically applying a time-varied gain to a first received response echo pulse and a second received response echo pulse to optimize the first received response echo pulse and the second received response echo pulse in regards to a range of the inspection device shown on the graphical user interface.

8. The method of claim 1 comprising:

providing a graphical user interface to the user, the graphical user interface capable of presenting to the user of the inspection device at least one depth indicator to indicate a depth corresponding to a location where the detected echo reflection occurs.

9. A material inspection device comprising:

an offset calculator, the offset calculator determining a thickness offset from calibration information, the calibration information identifying a time of flight of a pulse through a reference sample similar in composition to a material to be inspected, the thickness offset indicating when a thickness of a material being inspected differs from a thickness of the reference sample;

a memory unit, the memory unit storing the calibration information received by the data receiving unit and the thickness offset determined by the offset calculator;

a detector, the detector configured to detect a change in thickness of the material being inspected;

a calibration thickness alarm, the calibration thickness alarm set corresponding to the thickness offset stored in the memory unit, that when engaged, alerts a user of the device of a change in thickness of the material as detected by the detector; and an offset calculator, the offset calculator determining a damage offset from calibration information, the calibration information identifying a time of flight of a pulse through a reference sample similar in composition to a material to be inspected, the offset calculator using the damage offset to determine a thickness offset, the thickness offset indicating when a thickness of a material being inspected differs from a thickness of the reference sample.

10. The device of claim 9 wherein the detector comprises:

a pulse receiver to receive a response echo pulse from the material being inspected;

a calculator to calculate a time of flight for the received response echo pulse;

a comparison unit to compare the calculated time of flight with the damage offset and the thickness offset, stored in the memory unit, the comparison unit producing a result; and the detector that receives the result and detects a change in the thickness of the material being inspected when the result indicates that the calculated time of flight is greater than the damage offset and the thickness offset.

11. The device of claim 9 wherein the calibration thickness alarm comprises:

a graphical user interface, the graphical user interface visually presenting a calibration thickness alarm to a user of the device upon a change in thickness of the material as detected by the detector, the calibration thickness alarm set corresponding to the thickness offset stored in the memory unit.

12. The device of claim 11, wherein the graphical user interface visually presenting a calibration thickness alarm to a user of the device upon a change in thickness of the material as detected by the detector, the calibration thickness alarm set corresponding to the thickness offset stored in the memory unit, the graphical user interface also presenting a waveform of a received response echo pulse and the calibration information stored in the memory unit.

13. The device of claim 9 comprising:

a graphical user interface, the graphical user interface visually presenting a received response echo pulse and information concerning the material being inspected.

14. The device of claim 13 comprising:

an automatic gain controller configured to automatically amplify an amplitude of the received response echo pulse to optimize the received response echo pulse in regards to a range of the inspection device shown on the graphical user interface.

15. The device of claim 13 comprising:
a time varied gain controller configured to automatically apply a time-varied gain to a first received response echo pulse and a second received response echo pulse to optimize the first received response echo pulse and the second received response echo pulse in regards to a range of the inspection device shown on the graphical user interface.

16. The device of claim 9 comprising:
a graphical user interface, the graphical user interface capable of presenting to the user of the inspection device at least one depth indicator to indicate the depth corresponding to the location where a detected echo reflection occurs.

17. A computer program product, stored on computer readable medium, for alerting a user of a material inspection device of a change in thickness of a material being inspected, the computer program product comprising:
computer program code for determining a thickness offset from calibration information, the calibration information identifying a time of flight of a pulse through a reference sample similar in composition to a material to be inspected, the thickness offset indicating when a thickness of a material being inspected differs from a thickness of the reference sample;
computer program code for setting a calibration thickness alarm, the calibration thickness alarm corresponding to the thickness offset;
computer program code for detecting a change in thickness of the material being inspected;
computer program code for engaging the calibration thickness alarm to alert the user of the inspection device of a detected change in thickness of the material being inspected;
computer program code for determining a damage offset from calibration information, the calibration information identifying a time of flight of a pulse through a reference sample similar in composition to a material to be inspected; and
computer program code for determining a thickness offset from the damage offset, the thickness offset indicating when a thickness of a material being inspected differs from a thickness of the reference sample.

18. A computerized device comprising:
a memory;
a processor;
a display;
an input/output interface; and
an interconnection mechanism coupling the memory, the processor, and the input/output interface, allowing communication there between;
wherein the memory of the computerized device is encoded with a calibration thickness alarm application, that when executed in the processor, provides a calibration thickness alarm process that alerts a user of a material inspection device of a change in thickness of a material being inspected, by causing the computerized [system] device to perform operations of:
determining a thickness offset from calibration information, the calibration information identifying a time of flight of a pulse through a reference sample similar in composition to a material to be inspected, the thickness offset indicating when a thickness of a material being inspected differs from a thickness of the reference sample;
setting a calibration thickness alarm, the calibration thickness alarm corresponding to the thickness offset;
detecting a change in thickness of the material being inspected;
engaging the calibration thickness alarm to alert the user of the inspection device of a detected change in thickness of the material being inspected;
determining a damage offset from calibration information, the calibration information identifying a time of flight of a pulse through a reference sample similar in composition to a material to be inspected; and
determining a thickness offset from the damage offset, the thickness offset indicating when a thickness of a material being inspected differs from a thickness of the reference sample.

19. A method of alerting a user of a material inspection device of a change in thickness of a material being inspected, the method comprising:
determining a thickness offset from calibration information, the calibration information identifying a time of flight of a pulse through a reference sample similar in composition to a material to be inspected, the thickness offset indicating when a thickness of a material being inspected differs from a thickness of the reference sample;
setting a calibration thickness alarm, the calibration thickness alarm corresponding to the thickness offset;
detecting a change in thickness of the material being inspected;
engaging the calibration thickness alarm to alert the user of the inspection device of a detected change in thickness of the material being inspected;
providing a graphical user interface to the user, the graphical user interface capable of presenting a received response echo pulse and information concerning the material being inspected; and
automatically amplifying an amplitude of the received response echo pulse to optimize the received response echo pulse in regards to a range of the inspection device shown on the graphical user interface.

20. The method of claim 19 further comprising:
automatically applying a time-varied gain to a first received response echo pulse and a second received response echo pulse to optimize the first received response echo pulse and the second received response echo pulse in regards to a range of the inspection device shown on the graphical user interface.

21. A material inspection device comprising:
an offset calculator, the offset calculator determining a thickness offset from calibration information, the calibration information identifying a time of flight of a pulse through a reference sample similar in composition to a material to be inspected, the thickness offset indicating when a thickness of a material being inspected differs from a thickness of the reference sample;
a memory unit, the memory unit storing the calibration information received by the data receiving unit and the thickness offset determined by the offset calculator;
a detector, the detector configured to detect a change in thickness of the material being inspected;
a calibration thickness alarm, the calibration thickness alarm set corresponding to the thickness offset stored in the memory unit, that when engaged, alerts a user of the device of a change in thickness of the material as detected by the detector;

a graphical user interface, the graphical user interface visually presenting a received response echo pulse and information concerning the material being inspected; and an automatic gain controller configured to automatically amplify an amplitude of the received response echo pulse to optimize the received response echo pulse in regards to a range of the inspection device shown on the graphical user interface.

22. The device of claim 21 further comprising:

a time varied gain controller configured to automatically apply a time-varied gain to a first received response echo pulse and a second received response echo pulse to optimize the first received response echo pulse and the second received response echo pulse in regards to a range of the inspection device shown on the graphical user interface.

* * * * *